US008903497B2

(12) United States Patent
Norgaard et al.

(10) Patent No.: US 8,903,497 B2
(45) Date of Patent: Dec. 2, 2014

(54) CONFORMAL ANTENNA FOR IMPLANTABLE MEDICAL DEVICE AND IMPLANTABLE MEDICAL DEVICE WITH SUCH ANTENNA

(75) Inventors: Clark B. Norgaard, Phoenix, AZ (US); Michael W. Barror, Gilbert, AZ (US); Douglas D. Nippoldt, Centerville, MN (US); Tony A. Ulrich, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 486 days.

(21) Appl. No.: 12/895,083

(22) Filed: Sep. 30, 2010

(65) Prior Publication Data

US 2012/0081201 A1  Apr. 5, 2012

(51) Int. Cl.
*A61N 1/372* (2006.01)
*A61B 5/00* (2006.01)
*H01F 5/02* (2006.01)

(52) U.S. Cl.
CPC ............ *A61N 1/37229* (2013.01); *A61B 5/0031* (2013.01); *H01F 5/02* (2013.01); *A61N 1/37205* (2013.01)
USPC .......................................................... 607/60

(58) Field of Classification Search
CPC ................................................ A61N 1/37229
USPC .......................................................... 600/32
See application file for complete search history.

(56) References Cited

U.S. PATENT DOCUMENTS 6,496,733 B2 * 12/2002 Zarinetchi et al. .............. 607/36
6,931,284 B2    8/2005 Engmark et al.
7,363,087 B2    4/2008 Nghiem et al.
7,483,752 B2    1/2009 Von Arx et al.
7,554,493 B1    6/2009 Rahman
2006/0085041 A1  4/2006 Hastings et al.
2009/0036939 A1  2/2009 Singh et al.
2009/0222028 A1  9/2009 Dlugos, Jr. et al.

FOREIGN PATENT DOCUMENTS

EP      2 116 173 A1   11/2009
WO  WO 2004/059568 A1    7/2004

OTHER PUBLICATIONS

International Search Report and Written Opinion for PCT/US2011/047911.

* cited by examiner

*Primary Examiner* — Luther Behringer
(74) *Attorney, Agent, or Firm* — Michael J. Ostrom; Stephen W. Bauer (57) ABSTRACT

System and method for making an antenna. An implantable medical device has a housing, a bobbin and a coil. The housing has an interior generally tubular cross-section with a longitudinal axis, the housing having a lateral portion of a segment of the tubular cross-section along the longitudinal axis. The bobbin has a first side nearest to the interior of the housing and a second side opposite the first side. The coil, wound around the bobbin on a winding axis orthogonal to the longitudinal axis of the tubular cross-section, has a greater number of complete turns proximate the second side of the bobbin than proximate the first side of the bobbin, with the coil having a cross-sectional shape selected for a space between the bobbin and the interior of the housing in the lateral portion of the segment of the tubular cross-section along the longitudinal axis of the housing.

15 Claims, 10 Drawing Sheets

CONFORMAL ANTENNA FOR IMPLANTABLE MEDICAL DEVICE AND IMPLANTABLE MEDICAL DEVICE WITH SUCH ANTENNA

FIELD

The present invention is generally related to an antenna for an implantable medical device and an implantable medical having such an antenna and, particularly, an antenna for an implantable medical device conforming to space within the implantable medical device and an implantable medical having such an antenna.

BACKGROUND

Electrically active implantable medical devices such as pacemakers, cardioverter/defibrillators, neurological stimulators and drug pumps are well known in the art. Such implantable medical devices are commonly powered by an internal power source, such as a battery, and are controlled by an internal controller, such as a microprocessor. The controller commonly controls additional circuitry to deliver appropriate therapy to the patient in whom the device has been implanted and to sense the patient condition using internal sensors. Further, the controller commonly controls a wireless communication system which enables the implantable medical device to exchange information and commands with medical devices external to the patient, as well as other implantable medical devices.

Such implantable medical devices are definitionally configured to be placed and physically isolated within the patient. As such, the physical size of the implantable medical devices may have a significant impact both on the places within the patient where the implantable medical device may be implanted and on patient comfort and quality of life. While a relatively large implantable medical device may have to be placed somewhat far from the site of therapy delivery owing to lack of space within the patient's anatomy close to the site of therapy delivery, a relatively smaller device may be placed either closer to or directly at the site of therapy delivery. In addition, while a relatively large implantable medical device may require large incisions and displacement of patient tissue during implantation, a relatively small implantable medical device may be implanted using small incisions with little tissue displacement. Moreover, while a relatively small device may substantially physically unobtrusive to the patient's lifestyle, and even, if very small, physically undetectable for the patient, a relatively large device may create highly visible bulges in the patient's skin and may have a meaningful impact on the patient's lifestyle.

Thus, it is broadly in the interest of both the patient and the medical professionals who work with the implantable medical devices that such devices are made as small as can be achieved while still meeting important requirements for therapy capabilities and longevity. To that end, efficiencies in the sizing of implantable medical devices have been sought through reductions in size of physical components, including electronic components, mechanical components such as leads and chemical components such as batteries. In addition, the physical layout of such implantable medical devices have been adjusted to more efficiently pack components in space.

SUMMARY

However, past limitations on the ability to minimize the volume of implantable medical devices have been seen in the fact that the components of implantable medical devices are not commonly conformal. This is to say, there is little scope to change the three-dimensional shape of the components utilized in the implantable medical device. Most components may tend to be off-the-shelf components, rendering them effectively impossible to adjust in three-dimensional shape. And while custom designed components, such as batteries and high-voltage capacitors, historically, may have some scope to have a selectable three-dimensional shape, the ability to shape such components three-dimensionally may tend to run into physical limitations. Broadly speaking, a high-voltage capacitor may be adjustable in three-dimensional shape, but must still accommodate two conductors separated by a dielectric, which means the three-dimensional shape may only be adjusted within that limitation.

A custom component of implantable medical devices which has not historically been subject to considerable latitude in three-dimensional shape is the telemetry coil. Generally speaking, physical constraints have placed limits on the extent to which the three-dimensional shape of the telemetry coil may vary. Historically, unless the coil has had a generally regular shape the coil may not transmit and receive efficiently. In the past, a telemetry coil has tended to be generally circular on a horizontal plane with an even physical density on a vertical plane parallel with the primary axis of the coil. In other words, while the physical size of the coil may be varied, the telemetry coils have traditionally had little scope for being anything other than a generally circular coil with an even and consistent cross-section. Because of the regularity imposed, coils are among the custom-designed components which have not been subject to much adjustment in order to minimize the total volume of the implantable medical device. In such cases, where the shape of the coil is not substantially adjustable, the shape of the implantable medical device may substantially be adjusted to conform to the coil, and the overall shape of the implantable medical device may be relatively limited to disk-like shapes generally consistent in shape with that of the telemetry coil.

It has been determined, however, that an efficient coil design may be made which is not necessarily circular and having an even cross-section. In particular, coils have been developed which are generally non-circular and with an irregular cross-section but which still meet efficiency and performance requirements. Because of the availability of irregular shapes, such coils may be custom designed to conform to available space within the implantable medical device, in contrast with conventional telemetry coils where the shape of the implantable device may be adjusted to conform to the coil.

Because the coil may conform to the available space in the implantable medical device, the volume within the implantable medical device may be more efficiently utilized than may be possible with a non-conformal coil design. Thus, the implantable medical device may be made smaller and more compact by using a conformal telemetry coil. In addition, the shapes of the implantable medical devices may shift from being generally disk-shaped, like previous coils, to other shapes which may be conducive for use in a patient, such as elongate capsule shapes.

In an embodiment, an implantable medical device has a housing, a bobbin and a coil. The housing has an interior generally tubular cross-section with a longitudinal axis, the housing having a lateral portion of a segment of the tubular cross-section along the longitudinal axis. The bobbin has a first side nearest to the interior of the housing and a second side opposite the first side. The coil, wound around the bobbin on a winding axis orthogonal to the longitudinal axis of the tubular cross-section, has a greater number of complete turns proximate the second side of the bobbin than proximate the first side of the bobbin, with the coil having a cross-sectional shape selected for a space between the bobbin and the interior of the housing in the lateral portion of the segment of the tubular cross-section along the longitudinal axis of the housing.

In an embodiment, the implantable medical device further has a plurality of surface mount electrodes positioned on the second side of the bobbin electrically coupled to the coil.

In an embodiment, the tubular cross-section comprises a circular cross-section.

In an embodiment, the lateral portion of the segment of the tubular cross-section comprises less than one-half of the tubular cross-section.

In an embodiment, an exterior shape of the coil follows a contour of the interior portion of the lateral portion of the segment of the tubular cross-section.

In an embodiment, the bobbin forms an aperture configured to admit a surface-mount component.

In an embodiment, the aperture of the bobbin is cuboid.

In an embodiment, the aperture of the bobbin is a rectangular cuboid.

In an embodiment, an antenna for an implantable medical device having a housing having an interior generally tubular cross-section with a longitudinal axis, the housing having a lateral portion of a segment of the tubular cross-section along the longitudinal axis, has a bobbin and a coil. The bobbin has a first side nearest to the interior of the housing and a second side opposite the first side. The coil, wound around the bobbin on a winding axis orthogonal to the longitudinal axis of the tubular cross-section, has a greater number of complete turns proximate the second side of the bobbin than proximate the first side of the bobbin, with the coil having a cross-sectional shape selected for a space between the bobbin and the interior of the housing in the lateral portion of the segment of the tubular cross-section along the longitudinal axis of the housing.

In an embodiment, the antenna further has a plurality of surface mount electrodes positioned on the second side of the bobbin electrically coupled to the coil.

In an embodiment, a method makes an antenna for an implantable medical device a housing having an interior generally tubular cross-section with a longitudinal axis. A bobbin is constructed having a first side nearest to an interior of a lateral portion of a segment of a tubular cross-section along a longitudinal axis of the housing and a second side opposite the first side. A coil is wound around the bobbin on a winding axis orthogonal to the longitudinal axis of the tubular cross-section. The coil has a greater number of complete turns proximate the second side of the bobbin than proximate the first side of the bobbin and has a cross-sectional shape selected for a space between the bobbin and the interior of the housing in the lateral portion of the segment of the tubular cross-section along the longitudinal axis of the housing.

In an embodiment, the method has the further step of electrically coupling the coil to a plurality of surface mount electrodes positioned on the second side of the bobbin.

DESCRIPTION

Figure 1A:
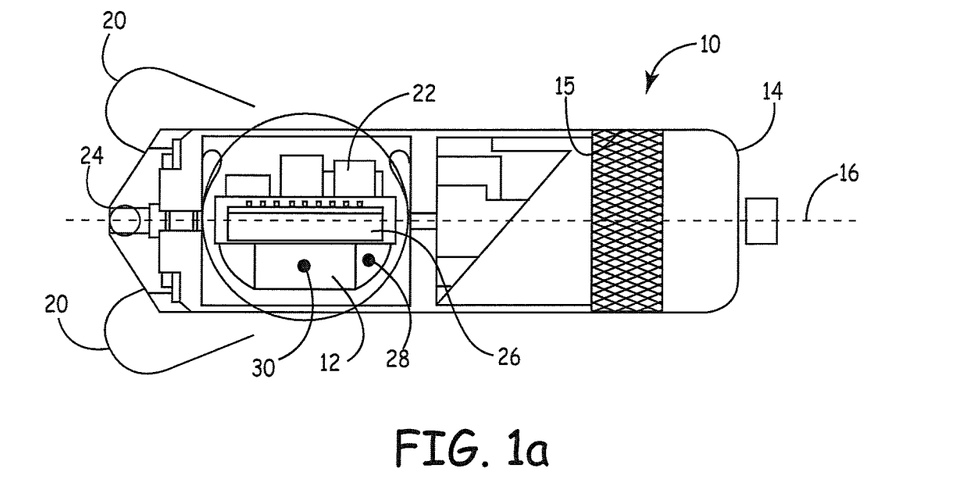
FIGS. 1a and 1b are cross-sectional views of an implantable medical device.
Figure 1B:
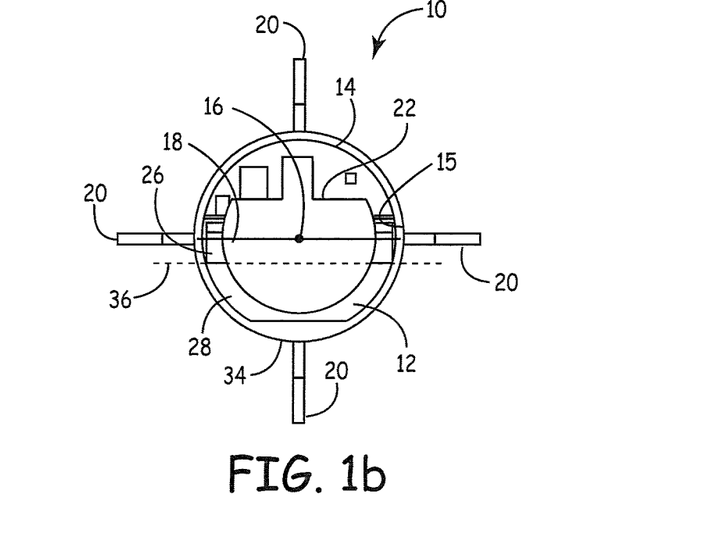
Figure 2A:
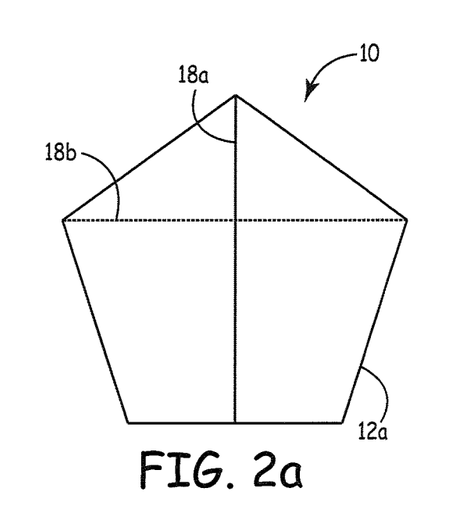
FIGS. 2a-2d depict alternative cross-sections for an implantable medical device.
Figure 2B:
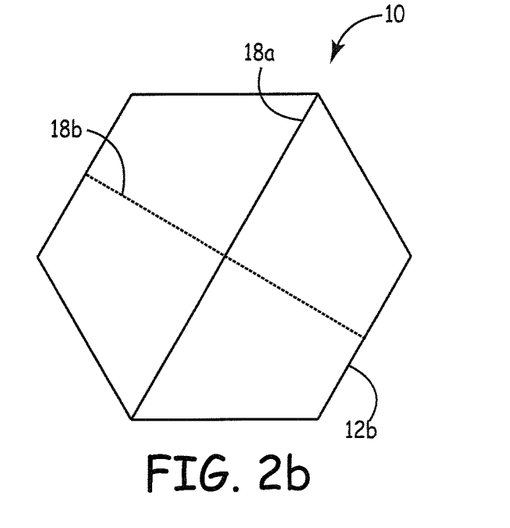
Figure 2C:
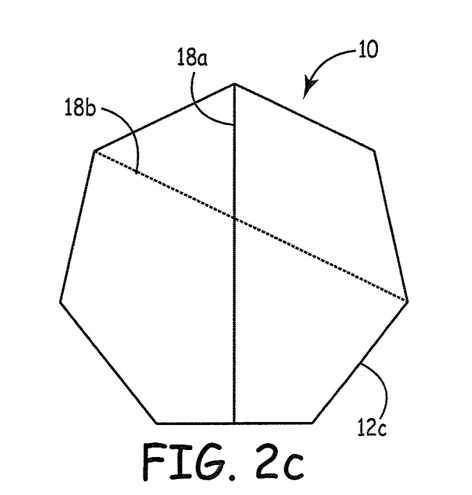
Figure 2D:
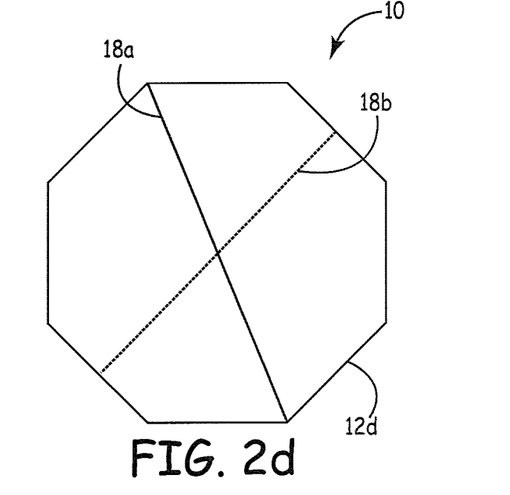

FIGS. 1a and 1b illustrates cross-sectional, cut-away views of implantable medical device 10 incorporating conformal telemetry antenna 12. In an embodiment, implantable medical device 10 is a pacemaker. In alternative embodiments, implantable medical device 10 is any active implantable medical device 10 known in the art or which may be designed in the future, including, but not limited to, cardioverter defibrillators, neurological stimulators and drug pumps. As illustrated, housing 14 is generally tubular with a cylindrical cross-section. In alternative embodiments, different cross-sectional shapes may be utilized, including oval, pentagonal, hexagonal, heptagonal and octagonal cross sections (shown in FIGS. 2a-2d below). In an embodiment, housing 14 has an outside diameter of twenty (20) French (approximately 6.7 millimeters) on the French gauge system and an inside surface 15. As illustrated, longitudinal axis 16 is longer than cross-sectional width 18. In alternative embodiments, longitudinal axis 16 is shorter than cross-sectional width 18.

FIGS. 2a-2d depict alternative cross sections for implantable medical device 10. As illustrated, FIG. 2a has housing 12a with pentagonal cross-section, FIG. 2b has housing 12b with hexagonal cross-section, FIG. 2c has housing 12c with heptagonal cross section and FIG. 2d has housing 12d with octagonal cross section. In such embodiments, cross-sectional width 18 may be defined in terms of conventions known in the art. In various embodiments, cross-sectional width 18a may be defined as the distance between vertices which are either directly opposing one another (as in FIGS. 2b and 2d), or between vertices which are nearly opposing one another (as in FIGS. 2a and 2c). In certain embodiments, alternative cross-sectional widths 18b may be drawn between opposing straight segments (as in FIGS. 2b and 2d) and between a directly opposing vertex and straight side (as in FIGS. 2a and 2c).

Returning to FIGS. 1a and 1b, tines 20 may capture patient tissue and secure implantable medical device 10 within the patient. In an embodiment, tines 20 are formed from a material such as a shape memory alloy and extended to a generally straight configuration for implantation. Upon implantation, tines 20 may coil and capture patient tissue within them, securing, at least in part, implantable medical device 10 relative to the patient tissue. Device componentry 22, such as batteries and electronic components such as controllers and therapy componentry are contained within housing 14 in positions not occupied by antenna 12. Inversely, antenna 12 may be positioned to occupy space not occupied by device componentry 22. Electrode 24 is operatively coupled to the therapy componentry may deliver an electrical therapeutic output generated by device componentry 22 to the patient. Antenna 12 and device componentry 22 are physically connected and operatively coupled to printed circuit board 26.

Antenna 12 includes coil 28 wound about bobbin 30 (obscured in FIG. 1b). Bobbin 30 incorporates surface mount electrodes 32 (obscured, see FIGS. 4a and 4b below) electrically coupled to coil 28 and configured to be coupled to printed circuit board 26 to electrically couple coil 28 to device componentry 22 and to mechanically secure antenna 12 within housing 14.

Figure 3:
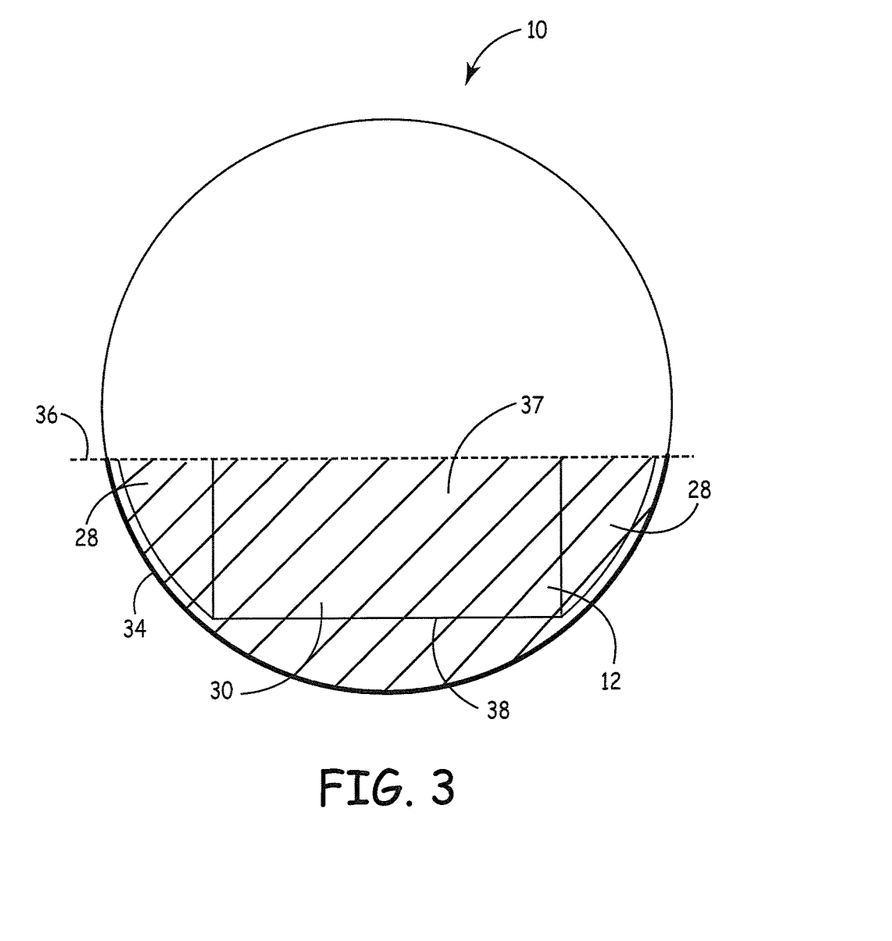
FIG. 3 is a simplified view of the cross-section of the implantable medical device of FIG. 1.

Coil 28 and bobbin 30 are configured so that antenna 12 consumes most of a volume of implantable medical device 10 defined by segment 34 of housing 14 and lateral portion 36 defined by a line connecting the ends of segment 34. This orientation is illustrated in FIG. 3, a simplified cross-sectional image of implantable medical device 10. Segment 34 (in bold) and lateral portion 36 combine to define cross-sectional segment area 37 (shown cross-hatched). As illustrated, the cross-section of antenna 12 substantially occupies all of cross-sectional area 37 by closely following the curve of segment 34 from lateral portion 36 to first side 38 of antenna 12. While the area of cross-sectional segment area 37 between first side 38 of antenna 12 and segment 34 is not occupied by antenna 12, owing to the need to wrap coil 28 about bobbin 30, and first side 38 is co-extensive with bobbin 30, the total cross-sectional area 37 is nevertheless substantially occupied by antenna 12. By extension, the volume defined by cross-sectional area 37 and a longitudinal length of antenna 12 is similarly substantially occupied by antenna 12. In an embodiment, antenna 12 occupies approximately eighty-three (83) percent of cross-sectional area 37 and approximately eighty (80) percent of the volume defined by cross-sectional area and a longitudinal length of antenna 12.

Figure 4A:
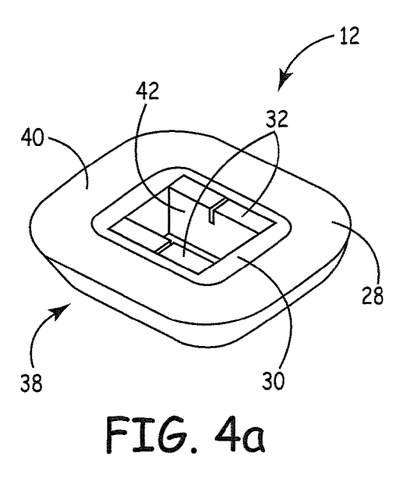
FIGS. 4a and 4b are illustrations of an antenna for the implantable medical device of FIGS. 1a and 1b.
Figure 4B:
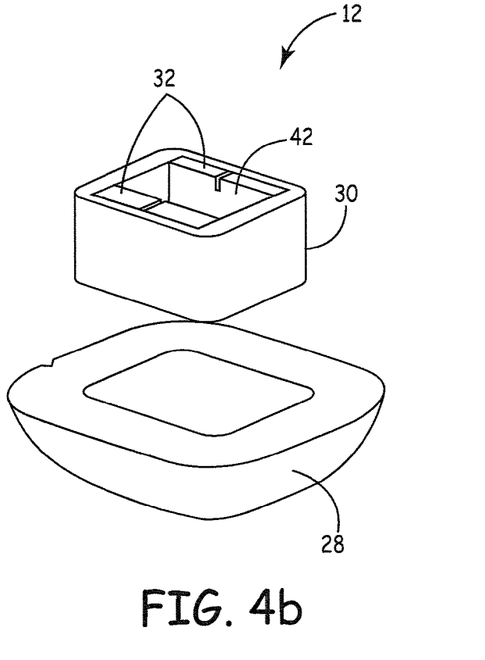

FIGS. 4a and 4b are un-exploded and exploded illustrations, respectively, of antenna 12. Coil 28 is wound about bobbin 30 so that coil 28 has fewer complete windings about bobbin 30 proximate first side 38 (obscured) of antenna 12 relative to second side 40 of antenna 12 so as to conform to the shape of cross-sectional area 37 while providing required telemetry performance for implantable medical device 10. In various embodiments incorporating the alternative cross-sections illustrated in FIGS. 2a-2d, for instance, coil 28 may be wound about bobbin 30 differently than as illustrated in FIGS. 4a and 4b so as to form a shape which conforms to fit into portions within housing 14 not occupied by device componentry 22 and other items contained within housing 14. In an embodiment, coil 28 has an inductance of approximately one thousand fifty-five (1,055) microHenries, a direct current resistance from approximately fifty (50) to approximately one hundred fifty (150) Ohms and a center frequency of approximately one hundred seventy-five (175) kilohertz.

Bobbin 30 may be formed from a variety of materials, including those which are non-conductive and/or non-ferromagnetic, such as a ceramic, a high temperature plastic and a phenolic resin. In an embodiment, bobbin 30 is formed from polyether ether ketone. In alternative embodiments, conductive material may be utilized for bobbin 30, though an insulative layer may be placed between coil 28 and bobbin 30 to prevent conduction from coil 28 to bobbin 30. As illustrated, bobbin 30 forms aperture 42. In alternative embodiments, bobbin 30 is solid or does not otherwise form aperture 42. In various embodiments, aperture 42 is sized to permit antenna 12 to be positioned on printed circuit board 26 such that one or more of device componentry 22 may fit within aperture 42. In one embodiment, aperture 42 is sized to admit a surface mount capacitor of device componentry 22. In some embodiments, aperture 42 may be cuboid in shape. In certain embodiments, aperture 42 is a rectangular cuboid. In an embodiment, aperture 42 has a two-dimensional area of approximately 0.252 square inches (1.625 square centimeters). In an embodiment, the two-dimensional area of aperture 42 has dimensions of approximately 0.12 inches (3.05 millimeters) by approximately 0.075 inches (1.90 millimeters) and a depth in bobbin 30 of approximately 0.63 inches (16.0 millimeters).

Figure 5A:
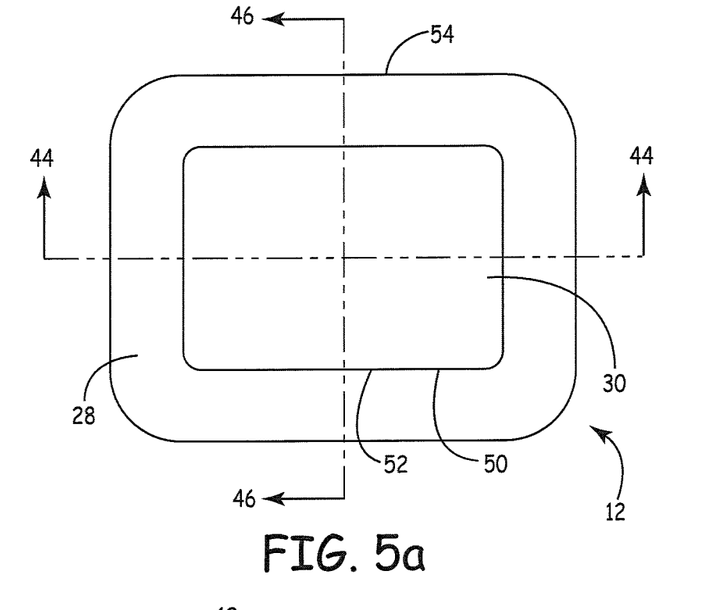
FIGS. 5a, 5b and 5c are profile drawings of the antenna of FIGS. 4a and 4b.
Figure 5B:
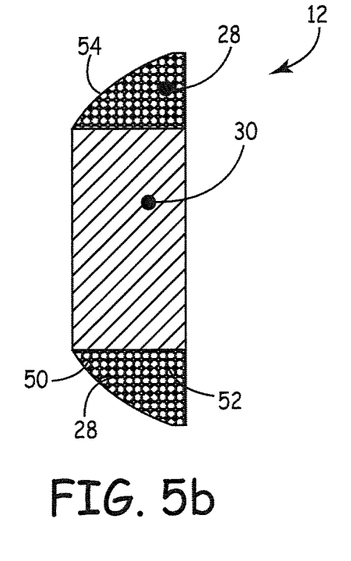
Figure 5C:
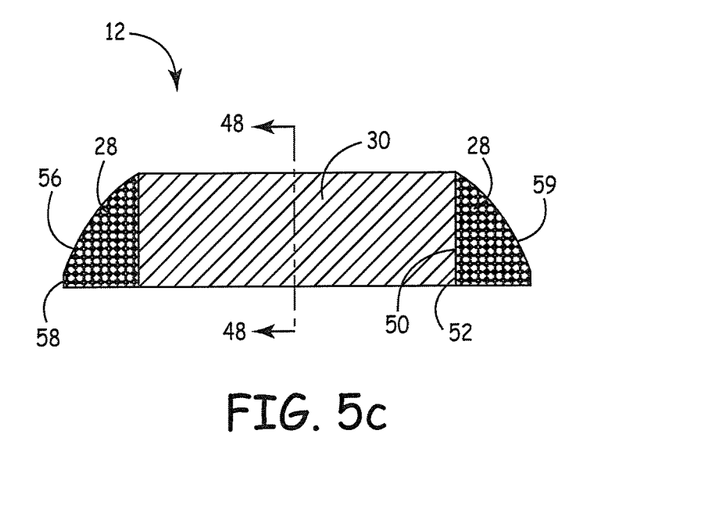

FIGS. 5a, 5b and 5c are profile drawings of antenna 12. Antenna 12 has longitudinal axis 44 corresponding to longitudinal axis 16 of housing 14, illustrated in section in FIG. 5b. Antenna 12 further has width axis 46, illustrated in section in FIG. 5c. Antenna 12 additionally has winding axis 48, illustrated in section in FIG. 5c. In an embodiment, antenna 12 is approximately 0.268 inches (6.81 millimeters) along longitudinal axis 44, 0.213 inches (5.41 centimeters) along width axis 46 and 0.062 inches (1.57 millimeters) in height along winding axis 48. In an embodiment, bobbin 30 has dimensions of outside surface 50 of approximately 0.185 inches (4.70 millimeters) along longitudinal axis 44, 0.130 inches (3.30 millimeters) along width axis 46 and a height of approximately 0.062 inches (1.57 millimeters) along winding axis 48. The outside dimensions of bobbin 30 are approximately the same as dimensions of inside surface 52 of coil 28 (illustrated here as a coil cross section without specifically showing individual windings, illustrated below with particularity in FIG. 6) wrapped around bobbin 30, as coil 28 is wrapped around bobbin 30.

Outside surface 54 of coil 28 occurs as a consequence of winding coil 28 around bobbin 30 in order to conform to housing 14 and incorporates curved section 56 and straight section 58. In various embodiments, straight section 58 prevents coil 28 from coming to a point proximate second side 40 of antenna 12 which may be relatively weak structurally in comparison with a remainder of coil 28. As illustrated, coil 28 is wound about bobbin 30 to create outside surface 54 which consumes available space in housing 14, as discussed above. In alternative embodiments, such as embodiments incorporated with cross-sections illustrated in FIGS. 2a-2d, outside surface 54 is either entirely curved or entirely straight in order to consume available space within the respective housings. In various embodiments, straight section 58 is co-planar with outside surface 50 of bobbin 30. In alternative embodiments, straight section 56 is angled with respect to outside surface 50. As illustrated, curved section 56 is curved to conform to inside surface 15 of housing 14. In an embodiment, curved section 56 has a radius of curvature of approximately 0.13 inches (3.30 millimeters). As illustrated, straight section 58 is approximately 0.008 inches (0.20 millimeters).

Figure 6:
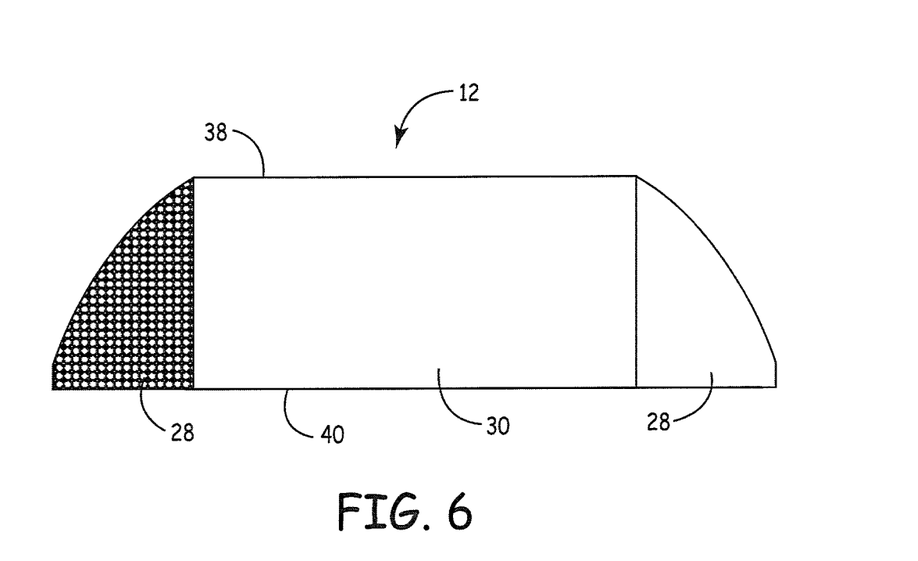
FIG. 6 is an image of winding detail of the antenna of FIGS. 4a and 4b.

FIG. 6 is an image of winding detail of coil 28. As discussed above, coil 28 has fewer windings proximate first side 38 of coil 28 than proximate second side 40 of coil 28. In an embodiment, to conform to the available space, coil 28 has only one (1) complete turn proximate first side 38 of bobbin 30. In an embodiment, to conform to the available space, coil 28 has twenty-one (21) complete turns proximate second side of bobbin 30. In an embodiment, coil 28 has a total of four hundred twenty-six (426) complete turns. In alternative embodiments, coil 28 has more than three hundred (300) complete turns. In an embodiment, to conform to the available space, coil 28 is made from approximately forty-five (45) gauge copper wire. In alternative embodiments, coil 28 is made from various alternative gauge wire made from various alternative materials known in the art. In certain embodiments, coil 28 is formed from alternative materials known in the art for use in telemetry coils.

Figure 7A:
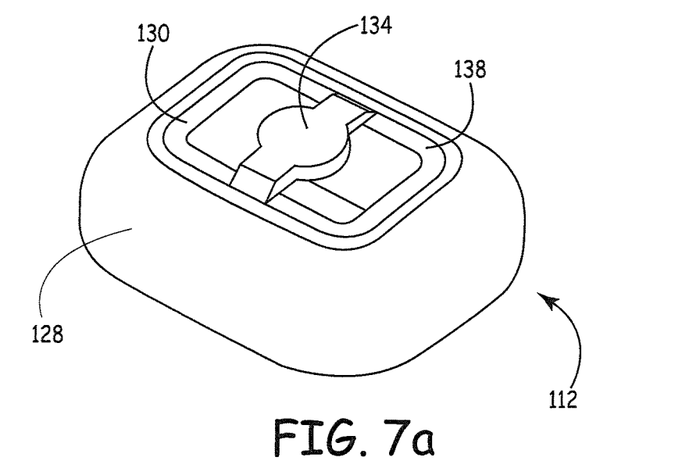
FIGS. 7a and 7b are illustrations of an alternative antenna for the implantable medical device of FIGS. 1a and 1b.
Figure 7B:
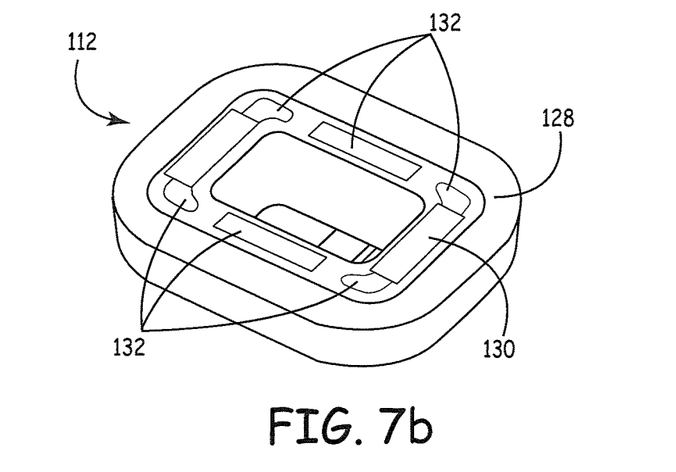

FIGS. 7a and 7b show top and bottom images of antenna 112, an alternative embodiment of antenna 12. Coil 128 provides approximately comparable electrical performance as coil 28. Bobbin 130 provides wider base 131, which allows for relatively more and larger surface mount electrodes 132.

Bobbin 130 further has top support 134 on first side 138. In an embodiment, top support 134 provides support during manufacturing of implantable medical device 10. Antenna 112 is configured to be utilized as a component of implantable medical device 10 consistent with the use of antenna 12.

Figure 8A:
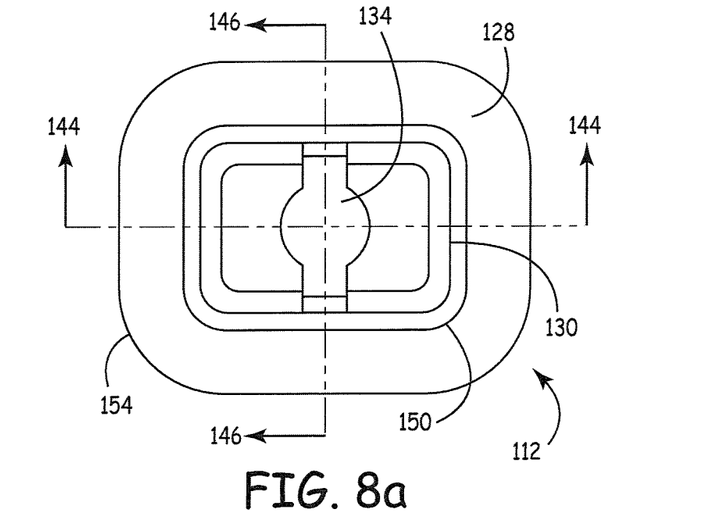
FIGS. 8a, 8b and 8c are profile drawings of the antenna of FIGS. 7a and 7b.
Figure 8B:
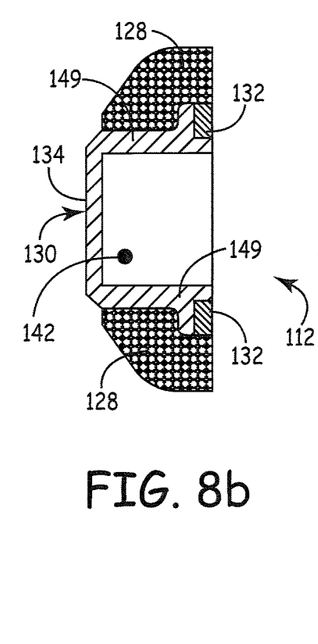
Figure 8C:
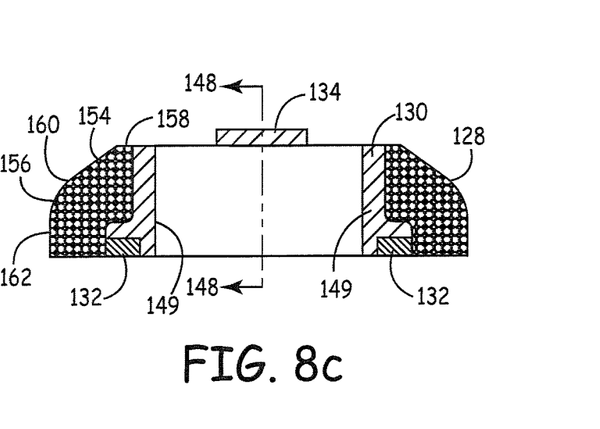

FIGS. 8a, 8b and 8c are profile drawings of antenna 112. Antenna 112 has longitudinal axis 144 corresponding to longitudinal axis 16 of housing 14, illustrated in section in FIG. 8c. Antenna 112 further has width axis 146, illustrated in section in FIG. 8b. Antenna 112 additionally has winding axis 148, illustrated in section in FIG. 8a. In an embodiment, antenna 112 is approximately 0.237 inches (6.02 millimeters) along longitudinal axis 144, 0.192 inches (4.88 millimeters) along width axis 146 and 0.063 inches (1.60 millimeters) in height along winding axis 148.

In an embodiment, bobbin 130 forms aperture 142 and has shoulder 149 incorporating surface mount electrodes 132. Bobbin 130 has dimensions of outside surface 150 of approximately 0.144 inches (3.66 millimeters) along longitudinal axis 144 without shoulder 149 and approximately 0.185 inches (4.70 millimeters) including shoulder 149, 0.099 inches (2.51 millimeters) along width axis 146 without shoulder 149 and approximately 0.130 inches (3.30 millimeters) with shoulder, and a height of approximately 0.062 inches (1.57 millimeters) along winding axis 148 without top support 134 and approximately 0.072 inches (1.83 millimeters) with top support 134.

Outside surface 154 of coil 128 incorporates curved section 156 between straight sections 158, 160, 162. In alternative embodiments, outside surface 154 is either entirely curved or entirely straight. In various embodiments, straight section 158 is approximately coplanar with first side 138 of bobbin 130 and straight section 162 is approximately orthogonal to first side 138 of bobbin 130. In such embodiments, straight surface 160 forms an angle of approximately thirty-six (36) degrees with respect to straight surface 158. In alternative embodiments, straight sections 158, 162 are angled with respect to first side 138. As illustrated, curved section 156 is curved to conform to inside surface 15 of housing 14. In an embodiment, curved section 156 has a radius of curvature of approximately 0.13 inches (3.30 millimeters).

Figure 9:
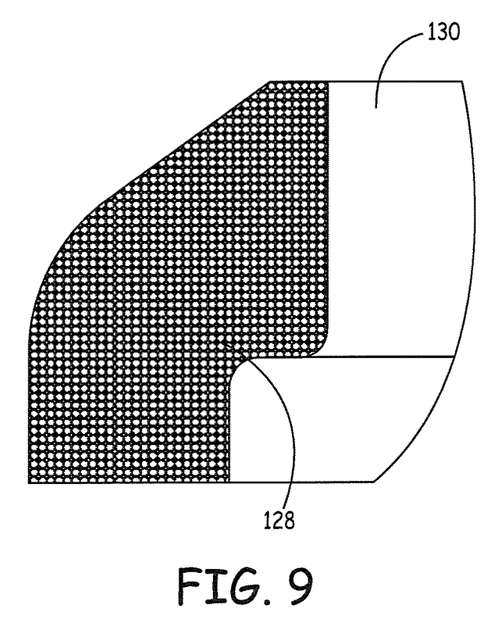
FIG. 9 is an image of winding detail of the antenna of FIGS. 7a and 7b.

FIG. 9 is an image of winding detail of coil 128. As discussed above, coil 128 has fewer windings proximate first side 138 of coil 128 than proximate second side 140 of coil 128. As illustrated, and in contrast with coil 28, coil 128 has windings staggered from row to row, with each winding being proximate six other windings, rather than in a grid pattern as illustrated in FIG. 6, with each winding being proximate four other windings. In an embodiment, coil 128 has only three (3) complete turn proximate first side 138 of coil 128. In an embodiment, coil 128 has eleven (11) complete turns proximate second side 140 of coil 128. In an embodiment, coil 128 has a total of four hundred eight-eight (488) complete turns. In alternative embodiments, coil 128 has more than three hundred (300) complete turns. In an embodiment, coil 128 is made from approximately forty-five (45) gauge copper wire. In alternative embodiments, coil 128 is made from various alternative gauge wire made from various alternative materials known in the art. In certain embodiments, coil 128 is formed from alternative materials known in the art for use in telemetry coils.

As has been discussed above, telemetry coils in implantable medical devices have historically been non-conformal to the available space in an implantable medical device housing, and have instead been generally circular or ovoid in shape and have the same thickness proximate a first major surface of the coil as proximate a second major surface of the coil. This has been the historic case because such antenna shapes and properties have tended to provide the best performance. It has been determined in empirical testing that, in spite of the nominally unconventional and inefficient layout and characteristics of antennas 12, 112, antennas 12, 112 provide performance surprisingly similar to otherwise similar telemetry coils configured according to more standard practices and which do not conform to available space. Thus, antennas such as non-conventional, conformal antennas 12, 112, have been found to be efficient replacements for conventionally shaped telemetry coils while incorporating the significant advantage of being conformal to available volume, thereby saving total volume for implantable medical device 10. In particular, it has been found that conformal antennas which have coils having complete winding in a ratio from three-to-eleven (3:11) from a first side (e.g., first side 38) to a second side (e.g., second side 40) to conformal antennas having complete winding from one-to-twenty-one (1:21) from the first side to the second side provide performance acceptably comparable to otherwise similar conventionally-shaped telemetry coils. In various embodiments, these ratios may be attained in view of limitations on the cross-sectional area of antenna 12 including the need to physically wind coil 28, the need for the wire or wires of coil 28 to physically remain in place after winding and a need to physically access bobbin 30 with wire and maintain a direct line of site between a rotating bobbin 30 and a spool of wire during the act of winding coil 28 around bobbin 30.

Figure 10:
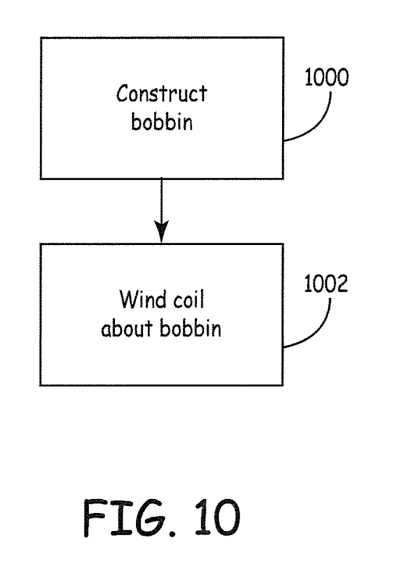
FIG. 10 is a flowchart for making an antenna.

FIG. 10 is a flowchart for making at least antenna 12 and, in various embodiments, antenna 112. Bobbin 30 is constructed (1000) with first side 38 configured to be positioned nearest to interior surface 15 of housing 14 relative to second side 40. Coil 28 is wound (1002) around bobbin 30 along winding axis 48 orthogonal to longitudinal axis 16 of housing 14. Coil 28 is wound so that a number of complete turns proximate first side 38 of bobbin 30 is greater than a number of complete turn proximate second side 40 of bobbin 30 and so that coil 28 has a cross-sectional shape selected for a space between bobbin 30 and interior 15 of housing 14 in lateral portion 36 of segment 34 of tubular cross-section of housing 14 along longitudinal axis 16 of housing 14.

Thus, embodiments of the conformal antenna for implantable medical device and implantable medical device with such antenna are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device, comprising:
   a housing having an interior surface having a generally tubular cross-section with a longitudinal axis, said housing having a lateral portion of a segment of said tubular cross-section along said longitudinal axis;
   an antenna within the housing, the antenna comprising:
      a bobbin within the housing, the bobbin having a first side and a second side opposite said first side, wherein the first side is nearer to the interior surface of said housing than that of the second side; and
      a coil wound around said bobbin, wherein said wound coil defines a winding axis extending from the first side of the bobbin to the second side of the bobbin and orthogonal to said longitudinal axis of said tubular cross-section, said coil having a greater number of complete turns proximate said second side of said bobbin than proximate said first side of said bobbin, with said coil having a cross-sectional shape selected for a space between said bobbin and said interior of said housing in said lateral portion of said segment of said tubular cross-section along said longitudinal axis of said housing.

2. The implantable medical device of claim 1 further comprising:
   device componentry within the housing; and
   a plurality of electrodes positioned on said second side of said bobbin, wherein the plurality of electrodes electrically couple said coil to said device componentry.

3. The implantable medical device of claim 1 wherein said tubular cross-section comprises a circular cross-section.

4. The implantable medical device of claim 3 wherein said lateral portion of said segment of said tubular cross-section comprises less than one-half of the tubular cross-section.

5. The implantable medical device of claim 4 wherein an exterior shape of said coil follows a contour of said interior portion of said lateral portion of said segment of said tubular cross-section.

6. The implantable medical device of claim 1 wherein said bobbin forms an aperture configured to admit a surface-mount component.

7. The implantable medical device of claim 6 wherein said aperture of said bobbin is cuboid.

8. The implantable medical device of claim 7 wherein said aperture of said bobbin is a rectangular cuboid.

9. The implantable medical device of claim 1 wherein an outside dimension of the bobbin is substantially the same as an inside dimension of the coil wrapped around the bobbin.

10. The implantable medical device of claim 1 wherein a length of the bobbin from the first side to the second side is less than a diameter of the tubular cross-section of the housing.

11. The implantable medical device of claim 10 wherein the length of the bobbin from the first side to the second side is less than half the diameter of the tubular cross-section of the housing.

12. The implantable medical device of claim 1 wherein the coil is wound along the winding axis across a length of the bobbin from the first side to the second side.

13. The implantable medical device of claim 1 wherein the coil is wound along the winding axis across a length of the bobbin running from the first side to the second side.

14. The implantable medical device of claim 1 wherein the bobbin is removable from the interior of the housing.

15. An implantable medical device comprising:
   a housing having an interior surface having a generally tubular cross-section with a longitudinal axis, said housing having a lateral portion of a segment of said tubular cross-section along said longitudinal axis;
   device componentry within the housing; and
   an antenna within the housing, the antenna comprising:
      a bobbin within the housing, the bobbin having a first side and a second side opposite said first side, wherein the first side is nearer to the interior surface of said housing than that of the second side;
      a coil wound around said bobbin, wherein said wound coil defines a winding axis extending from the first side of the bobbin to the second side of the bobbin and orthogonal to said longitudinal axis of said tubular cross-section, said coil having a greater number of complete turns proximate said second side of said bobbin than proximate said first side of said bobbin, with said coil having a cross-sectional shape selected for a space between said bobbin and said interior of said housing in said lateral portion of said segment of said tubular cross-section along said longitudinal axis of said housing; and
   at least one electrode positioned on said second side of said bobbin, wherein the at least one electrode electrically couples said coil to said device componentry.

* * * * *